(12) United States Patent
Kiyota et al.

(10) Patent No.: US 8,917,347 B2
(45) Date of Patent: Dec. 23, 2014

(54) FOCUS CONTROL METHOD AND CULTURE OBSERVATION APPARATUS

(75) Inventors: Yasujiro Kiyota, Tokyo (JP); Yoichi Wada, Kawasaki (JP); Hiroaki Kii, Fujisawa (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 13/290,565

(22) Filed: Nov. 7, 2011

(65) Prior Publication Data

US 2012/0120302 A1 May 17, 2012

Related U.S. Application Data

(63) Continuation of application No. PCT/JP2010/057789, filed on May 7, 2010.

(30) Foreign Application Priority Data

May 8, 2009 (JP) ................................ 2009-113396

(51) Int. Cl.
| | |
|---|---|
| *G03B 13/00* | (2006.01) |
| *H04N 5/232* | (2006.01) |
| *G02B 21/24* | (2006.01) |
| *G02B 7/38* | (2006.01) |

(52) U.S. Cl.
CPC .............. *G02B 21/244* (2013.01); *G02B 7/38* (2013.01)
USPC ............. 348/353; 348/79; 359/383; 359/392; 359/393; 250/201.3

(58) Field of Classification Search
USPC ............ 348/79, 353, 345; 359/383, 392, 393; 250/201.3
See application file for complete search history.

(56) References Cited

U.S. PATENT DOCUMENTS

| | | | |
|---|---|---|---|
| 5,398,096 A | 3/1995 | Yagoto | |
| 6,416,959 B1 * | 7/2002 | Giuliano et al. | ............... 435/7.2 |
| 7,968,832 B2 | 6/2011 | Okuda et al. | |
| 2002/0089740 A1 * | 7/2002 | Wetzel et al. | ................. 359/385 |

(Continued)

FOREIGN PATENT DOCUMENTS

| | | |
|---|---|---|
| JP | 56-2565 | 1/1981 |
| JP | 1991-166081 | 7/1991 |

(Continued)

OTHER PUBLICATIONS

PCT International Search Report mailed Jul. 13, 2010 in corresponding International Application No. PCT/JP2010/057789.

(Continued)

*Primary Examiner* — Paul Berardesca

(57) ABSTRACT

The focus control culture observation apparatus enable simple and reliable detection of a focusing position of an objective lens on a subject and with certainty. When a focusing position is detected, an area, which includes an edge portion of the culture medium drop is selected as an AF area which is to be a target of detecting the focusing position of the objective lens on the culture medium drop. The apparatus detects the focusing position on the culture medium drop based on an observation image of the AF area. By detecting the focusing position as a targeting area that is different from an area which is near the edge of the culture container and where illumination unevenness is generated, the detection accuracy can be improved.

15 Claims, 9 Drawing Sheets

(56) References Cited

U.S. PATENT DOCUMENTS

| | | |
|---|---|---|
| 2006/0000962 A1 | 1/2006 | Imabayashi et al. |
| 2007/0263997 A1* | 11/2007 | Hirai et al. .................... 396/123 |
| 2008/0247742 A1 | 10/2008 | Asano |
| 2009/0002540 A1* | 1/2009 | Suzuki et al. ............ 348/333.05 |
| 2009/0068728 A1 | 3/2009 | Kiyota |
| 2009/0086314 A1* | 4/2009 | Namba et al. ................. 359/383 |
| 2009/0195688 A1* | 8/2009 | Henderson et al. ........... 348/345 |
| 2009/0226061 A1 | 9/2009 | Maiya |

FOREIGN PATENT DOCUMENTS

| | | |
|---|---|---|
| JP | 5-346537 | 12/1993 |
| JP | 6-98232 | 4/1994 |
| JP | 2005-207986 | 8/2005 |
| JP | A-2006-003653 | 1/2006 |
| JP | 2006-309088 | 11/2006 |
| JP | 2008-139579 | 6/2008 |
| JP | 2008-257004 | 10/2008 |
| WO | 2007/145091 | 12/2007 |
| WO | 2008/007725 | 1/2008 |

OTHER PUBLICATIONS

Notification of Reasons for Refusal to corresponding Japanese patent application 2011-512361 dated Apr. 3, 2014.

* cited by examiner

FOCUS CONTROL METHOD AND CULTURE OBSERVATION APPARATUS

CROSS-REFERENCE TO RELATED APPLICATION

This application is related to and claims the benefit of priority from International Application PCT/JP2010/057789, filed May 7, 2010 which claims foreign priority benefit to Japanese Application No. 2009-113396 filed May 8, 2009, the disclosures of which are incorporated herein by reference.

BACKGROUND OF THE INVENTION

1. Technical Field

The present invention relates to a focus control method and a culture observation apparatus, and more particularly to a focus control method and a culture observation apparatus that can suitably be used for observing a subject floating in a culture medium drop.

2. Background Art

A focus control method of the present invention is a focus control method for detecting a focusing position of a subject in a culture container, this method including: an area specification step of specifying a detection area which includes a subject in the culture container; an AF area setting step of selecting and setting an AF area, which does not include an area located within a predetermined distance from an edge of the culture container and includes a boundary portion of the subject, out of the detection area; and a focal position detection step of detecting, by a focal position detection unit, a focusing position on the subject in the AF area.

A culture observation apparatus of the present invention is a culture observation apparatus having a microscope for observing a transparent culture container in which a culture medium drop is disposed, this apparatus having: an objective lens of the microscope; an observation unit for imaging the culture medium drop via the objective lens and generating an observation image; a specification operation unit for specifying a detection area which includes the culture medium drop in the culture container; an area setting unit for selecting an AF area, which does not include an area located within a predetermined distance from an edge of the culture container and includes a boundary portion of the culture medium drop, out of the detection area; and a focal position detection unit for detecting a focusing position on the culture medium drop in the AF area.

In the cell culture system however, it is difficult to detect a focusing position on the cells without operation of the observer, so in the cell culture system often the objective lens is moved based on the focal position specified by the observer in advance, and a plurality of observation images is captured. In other words, in the cell culture system, the objective lens is moved along the optical axis thereof from the specified focal position as the center, and observation images are captured at each position of the objective lens.

This is based on the assumption that if the observer specifies a position of the objective lens to be focused on the cells, as the focal position, and if the objective lens is moved to each position from this focal position as the center to capture observation images, then an observation image focused on the cells should be obtained.

Patent Document 1: Japanese Patent Application Laid-Open No. 2007-6841

In the case when an observation surface of the observation target in the cell culture system is relatively stable, such as a case of an adhesive cell, it is highly possible to obtain an observation image focusing on the cell, if a plurality of observation images is captured while moving the position of the objective lens. However in the case when the observation target is a floating cell, it may be difficult to obtain an observation image focused on the cell, even if a plurality of observation images is captured while moving the position of the objective lens.

For example, in a clinic where external fertilization is performed, a culture medium drop may be disposed on a dish, and a fertilized embryo may be cultured in the culture medium drop. In such a case, the fertilized embryo freely moves in the culture medium drop, hence it is impossible to specify in advance a position of the objective lens at which the fertilized embryo enters the observation field of view, and at which the fertilized embryo is focused. Therefore in the cell culture system, it has been difficult to automatically observe a fertilized embryo without operation of the observer.

Particularly if the culture medium drop is near the edge of the dish, illumination unevenness is generated since light is eclipsed on the side wall face of the dish, hence it is difficult to detect a position of the objective lens where the fertilized embryo is focused on.

DISCLOSURE OF THE INVENTION

With the foregoing in view, it is an object of the present invention to detect a focusing position of an objective lens on the subject simply and with certainty.

A focus control apparatus of the present invention is a focus control apparatus for detecting a focusing position of an objective lens on a subject, this apparatus including: an area setting unit that selects an area, which does not include an area located within a predetermined distance from an edge of a container placed on a stage and includes a boundary portion of the subject in the container, as a first target area which is to be a target of detecting the focusing position; an imaging control unit that changes a distance between the objective lens and the stage in a direction of an optical axis of the objective lens, and also captures a plurality of observation images on the first target area at different distances; and a focusing position detection unit that detects the focusing positions based on the plurality of observation images.

A culture observation apparatus of the present invention is a culture observation apparatus for observing a fertilized embryo in a culture medium drop and culturing the fertilized embryo, this apparatus having: an area setting unit that sets an area which includes an edge of the culture medium drop in a culture container as a detection area; a focusing position detection unit that detects a focusing position in the detection area; a specifying unit that obtains an observation image by imaging the culture medium drop based on the focusing position detected by the focusing position detection unit and specifies a position of the fertilized embryo in the culture medium drop based on the observation image; and an observation control unit that observes the fertilized embryo based on the position of the fertilized embryo.

According to the present invention, a focusing position of an objective lens on a subject can be detected simply and with certainty.

These together with other aspects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

These and/or other aspects and advantages will become apparent and more readily appreciated from the following description of the embodiments, taken in conjunction with the accompanying drawings of which.

DETAILED DESCRIPTION INCLUDING BEST MODE FOR CARRYING OUT THE INVENTION

Embodiments of the present invention will now be described with reference to the drawings.

Figure 1:
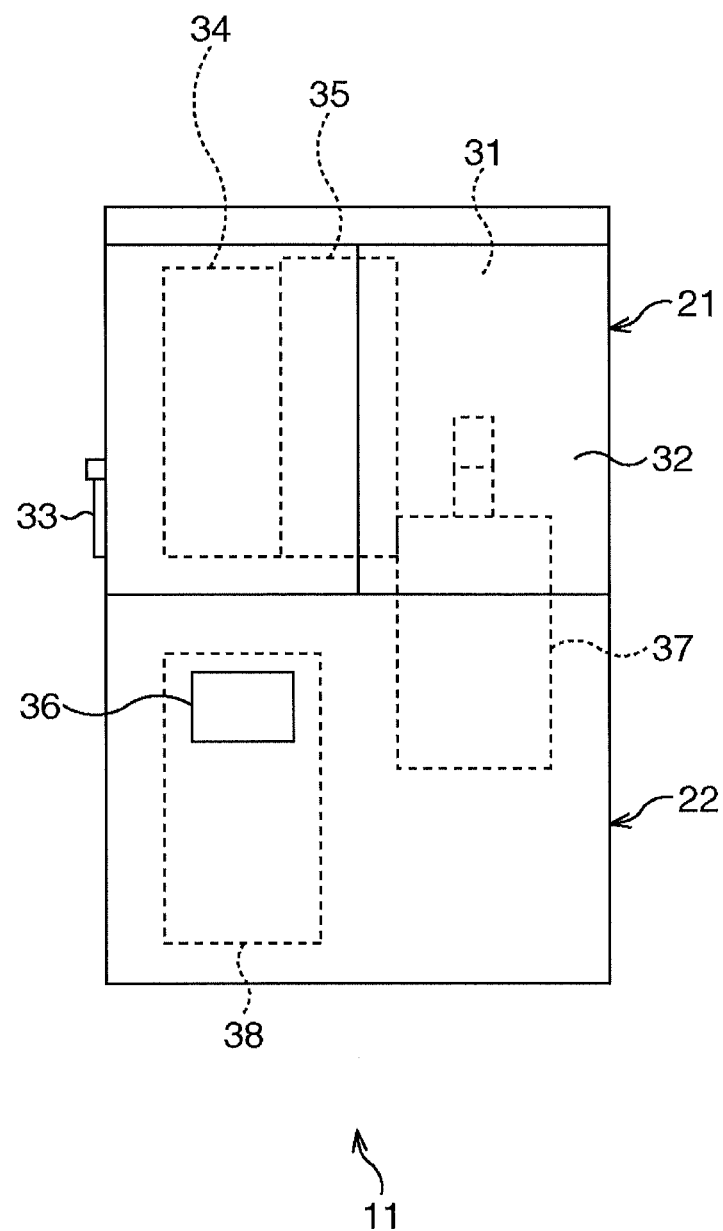
FIG. 1 is a front view depicting a general configuration of a culture observation apparatus to which the present invention is applied.

FIG. 1 is a front view depicting a general configuration of a culture observation apparatus to which the present invention is applied. In FIG. 1, the solid line indicates a structure of a portion which can be seen from the outside, and a broken line indicates a structure of an internal portion which cannot be seen from the outside.

The culture observation apparatus 11 is comprised of a first housing 21 for culturing a fertilized embryo to be an observation target, and a second housing 22 constituting the focus control apparatus, and the first housing 21 is used in a state of being placed on top of the second housing 22.

A thermostatic chamber 31 covered with a heat insulating material is created inside the first housing 21, and the thermostatic chamber 31 is connected with the outside via a front door 32 disposed on a front face of the first housing 21 and a transporting port 33, which is disposed on the left side face when viewed from the front of the first housing 21. A stocker 34 for holding a culture container, which is not illustrated, where the fertilized embryo is placed, and a container transporting mechanism 35 for transporting the culture container, are disposed in the thermostatic chamber 31 of the first housing 21.

In the second housing 22, a display unit 36 for displaying an observation image obtained by imaging a fertilized embryo in the culture container, for example, is displayed, and a control unit 38 for controlling the entire culture observation apparatus 11, and an observation unit 37 for observing the fertilized embryo and imaging the observation image are disposed.

The display unit 36 is disposed on the front side surface of the second housing 22, and is constituted by a liquid crystal display, for example. The observation unit 37 is constituted by a microscope, for example, and is secured such that a part of the unit protrudes into the thermostatic chamber 31.

Figure 2:
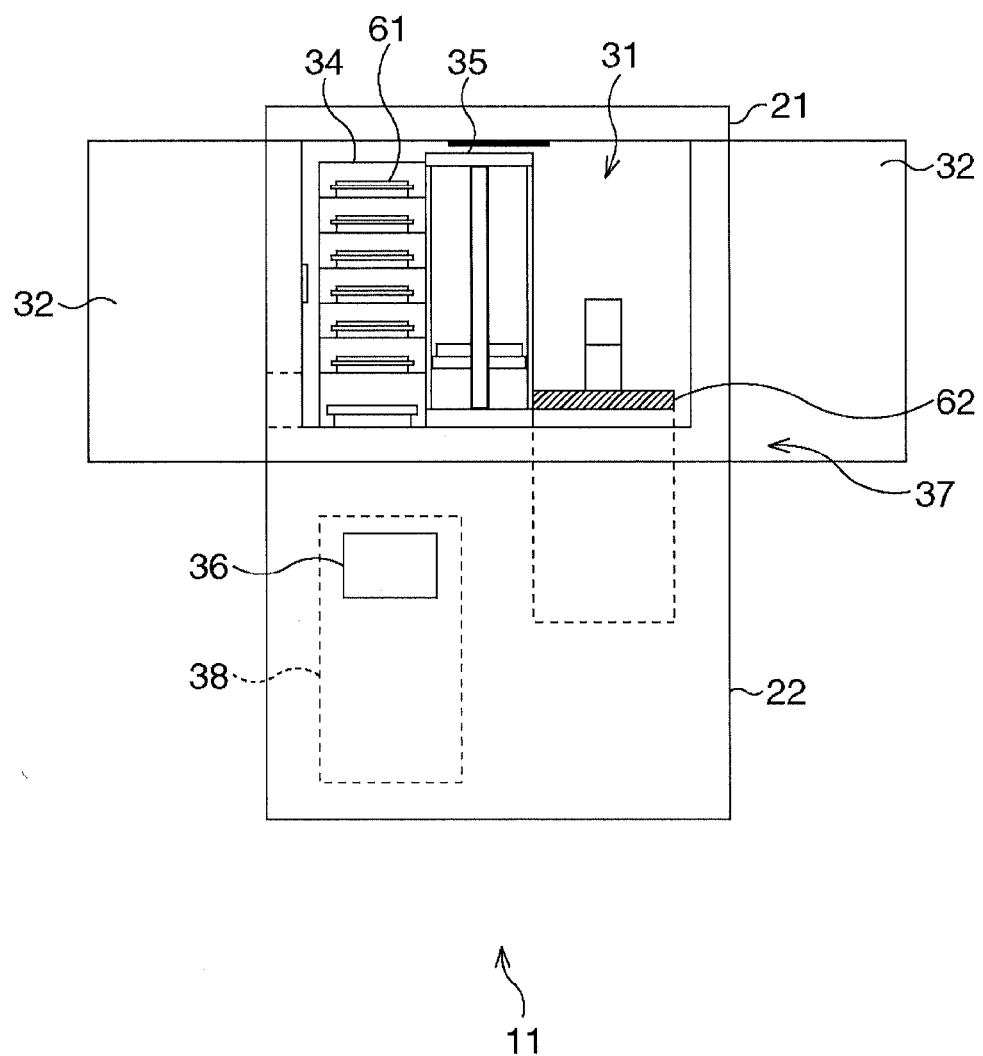
FIG. 2 is a diagram depicting a configuration example inside a first housing.

As FIG. 2 shows, the observer can place a culture container 61 on a stocker 34, or remove a culture container 61 from the stocker 34 by opening the front door 32. There are a plurality of racks in the stocker 34, and one or a plurality of culture container(s) 61 can be stored in each rack. Here a culture container 61 is a dish, for example, in which an observation target fertilized embryo is placed.

A stage 62, on which a culture container 61 is placed, is disposed in the observation unit 37, and the stage 62 is positioned near the container transporting mechanism 35 in the thermostatic chamber 31. The container transporting mechanism 35 transports a specified culture container 61 from the stocker 34 onto the stage 62, or transports a culture container 61 on the stage 62 onto a predetermined rack of the stocker 34 according to the control of the control unit 38.

Figure 3:
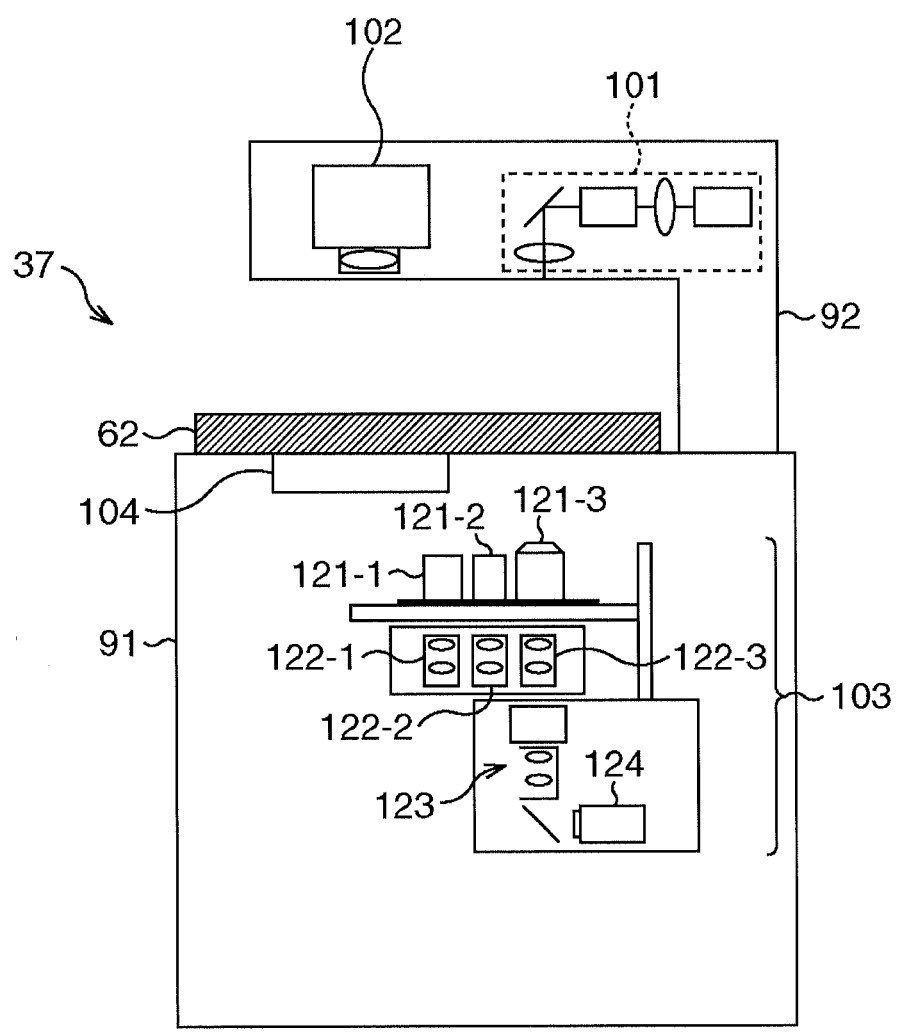
FIG. 3 is a diagram depicting a configuration example of an observation unit.

FIG. 3 shows a more detailed configuration of the observation unit 37 in FIG. 2.

As illustrated, the observation unit 37 is comprised of a main unit 91, a stage 62 and an arm 92, and the stage 62 and the arm 92 are disposed above the main unit 91 in FIG. 3. In the observation unit 37, the stage 62 and the arm 92 are disposed in the thermostatic chamber 31 of the first housing 21, and the main unit 91 is disposed in the second housing 22.

The stage 62 is constituted by a translucent material, and as shown in the figure moves in the vertical direction (hereafter z direction) and directions perpendicular to the z direction (hereafter xy directions) according to the control of the control unit 38.

The arm 92 has a surface facing the surface of the stage 62, and a first illumination unit 101 and a container observation unit 102 are disposed on the arm 92 at positions facing the stage 62.

The first illumination unit 101 comprises a light source which emits illumination light to illuminate a fertilized embryo to be observed, and an illumination optical system for irradiating the illumination light from the light source onto the culture container 61 on the stage 62, and as shown in the figure the illumination light is irradiated onto the culture container 61 from the top. The first illumination unit 101 is used when the phase contrast observation is performed on the fertilized embryo in the culture container 61.

The container observation unit 102 comprises an image optical system which forms an image of light which entered from the culture container 61 on the stage 62, and a camera which captures an observation image of a fertilized embryo as a subject, by receiving the light collected by the image optical system, and performing photoelectric conversion. The container observation unit 102 is used when the fertilized embryo is observed using the bright field observation.

A microscopic observation unit 103, which faces the first illumination unit 101, and a second illumination unit 104, which faces the container observation unit 102, are disposed in the main unit 91. The microscopic observation unit 103 is used for phase contrast observation of the fertilized embryo, and the second illumination unit 104 is used for bright field observation of the fertilized embryo.

A plurality of objective lenses 121-1 to 121-3, having a different optical magnification from one another, and a plurality of intermediate zoom lenses 122-1 to 122-3, are disposed in the microscopic observation unit 103.

The objective lens 121-1 and the intermediate zoom lens 122-1 are disposed on the optical path of the illumination light from the first illumination unit 101 (hereafter called "phase contrast observation optical path") when the fertilized embryo is observed at ×2 magnification. When the fertilized embryo is observed at ×4 magnification, the objective lens 121-2 and the intermediate zoom lens 122-2 are disposed on the phase contrast observation optical path, and when the fertilized embryo is observed at ×10 magnification, the objective lens 121-3 and the intermediate zoom lens 122-3 are disposed on the phase contrast observation optical path.

In other words, when the fertilized embryo is observed using the phase contrast observation, one combination out of the objective lens 121-1 and the intermediate zoom lens 122-1, the objective lens 121-2 and the intermediate zoom lens 122-2, and the objective lens 121-3 and the intermediate zoom lens 122-3, is disposed on the phase contrast observation optical path, according to the observation magnification.

If it is not necessary to distinguish the object lenses 121-1 to 121-3 from one another, then these objective lenses may be simply referred to as "objective lens 121", and if it is not necessary to distinguish the intermediate zoom lenses 122-1 to 122-3 from one another, then these intermediate zoom lenses may be simply referred to as "intermediate zoom lens 122".

Under the objective lens 121 and the intermediate zoom lens 122 in the microscopic unit 103, an image optical system 123 and a camera 124 are disposed as illustrated. The image optical system 123 collects illumination light which entered from the intermediate zoom lens 122, and guides the illumination light into the camera 124, and the camera 124 receives the illumination light which entered from the image optical system 123 and performs photoelectric conversion, so as to capture an observation image of the fertilized embryo as the subject.

Therefore in the case of the phase contrast observation of the fertilized embryo, the illumination light from the first illumination unit 101 is irradiated onto the culture container 61 on the stage 62, and the illumination light transmitted through the culture container 61 passes through the objective lens 121 and the image optical system 123, and is received by the camera 124.

The second illumination unit 104 of the main unit 91 comprises: a light source for emitting illumination light, and an illumination optical system for irradiating the illumination light from the light source onto the culture container 61 on the stage 62. The second illumination unit 104 is used for performing the bright field observation on the entire culture container 61 of the fertilized embryo. In other words, in order to perform the bright field observation for the entire culture container 61 of the fertilized embryo, the illumination light from the second illumination unit 104 is irradiated onto the culture container 61 on the stage 62, and the illumination light transmitted through the culture container 61 is received by the container observation unit 102.

Figure 4:
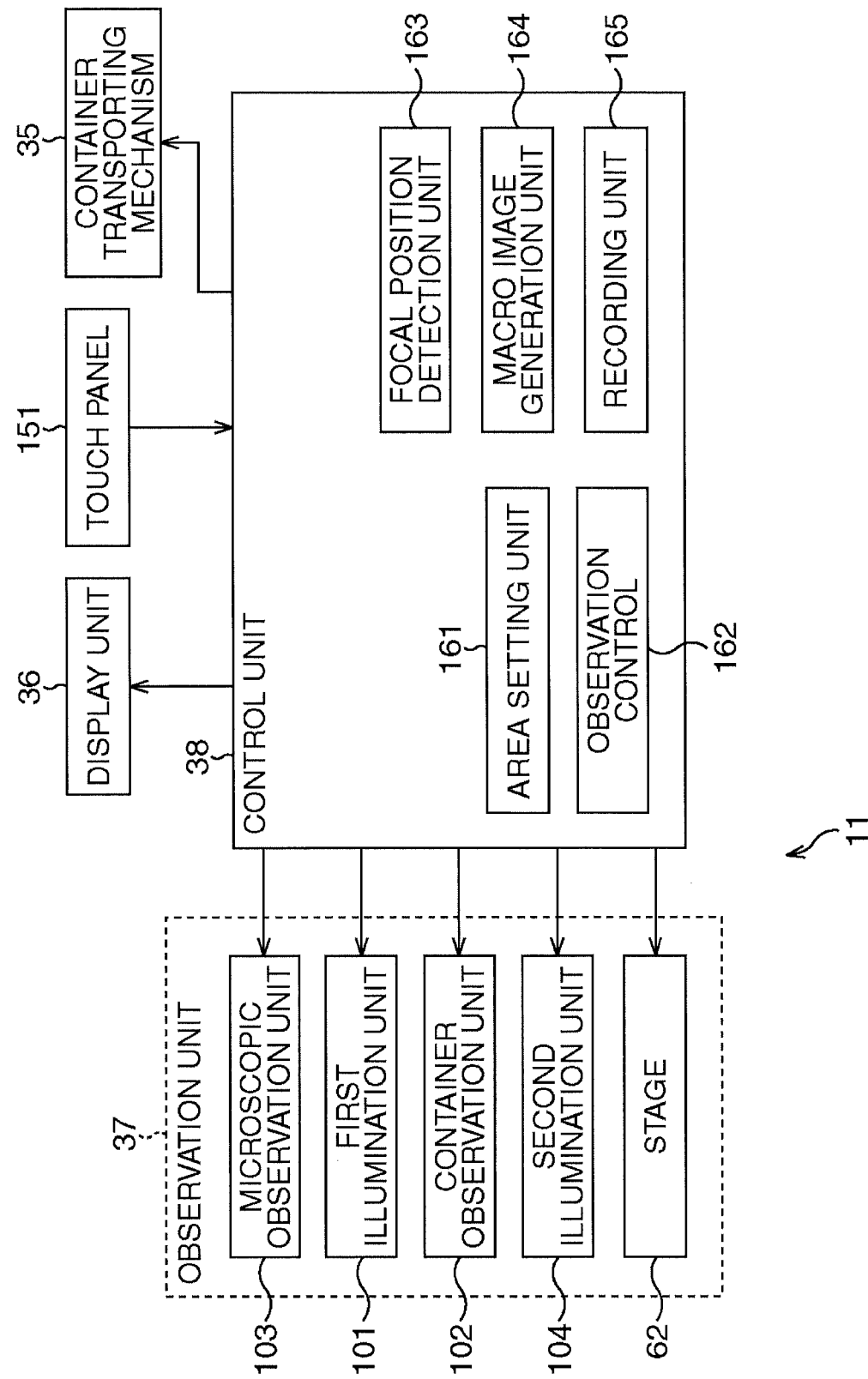
FIG. 4 is a diagram depicting a functional configuration example of the culture observation apparatus.

FIG. 4 is a diagram depicting a functional configuration example of the culture observation apparatus 11. In FIG. 4, a composing element the same as that in FIG. 2 or FIG. 3 is denoted with a same reference numeral, for which description is omitted unless necessary.

In the example in FIG. 4, the stage 62, the first illumination unit 101 to the second illumination unit 104, the display unit 36, the container transporting mechanism 35 and the touch panel 151 are connected to the control unit 38. The touch panel 151 is superposed on the display screen of the display unit 36, and detects the contact of the observer on the display screen, the touch panel 151 to be more precise, of the display unit 36, and supplies a signal to indicate the contact position to the control unit 38. For example, the observer can perform input operation by touching the touch panel 151, and instruct the execution of various processings through this input operation.

Based on a signal supplied from the touch panel 151, the control unit 38 displays an observation image on the display unit 36, or controls operation of the observation unit 37 and the container transporting mechanism 35. The control unit 38 has an area setting unit 161, an observation control unit 162, a focal position detection unit 163, a macro image generation unit 164 and a recording unit 165.

The area setting unit 161 sets an AF (Auto Focus) area for detecting a focusing position of the objective lens 121 to focus on a subject to be an observation target, that is, a position of the objective lens 121 when the focal position of the objective lens 121 is located at the subject.

In other words, the AF area is an area used for detecting a focusing position by auto focus control, out of the area on the culture container 61, and the AF area may have the same size and the same shape as the observation field of view of the objective lens 121, or may be a smaller area than the observation field of view of the objective lens 121. For example, if the AF area has a same shape and a same area as the observation field of view of the objective lens 121, the entire observation image that was captured becomes the AF area, and if the AF area is smaller than the observation field of view of the objective lens 121, a predetermined area of the observation image is set as the AF area.

The observation control unit 162 controls operation of each component of the observation unit 37 and the container transporting mechanism 35. The focal position detection unit 163 detects a focusing position of the objective lens 121 on the subject based on the AF area which is set by the area setting unit 161 and the captured observation image.

The focusing position of the objective lens 121 on the subject in this case refers to a relative position of the objective lens 121 with respect to the stage 62 in the z direction (optical axis direction of the objective lens 121) when the focal point (focal plane) of the objective lens 121 is located on the subject (e.g. fertilized embryo). In the culture observation apparatus 11, the objective lens 121 is fixed, and the stage 62 moves in the z direction, hence the focusing position of the objective lens 121 is represented by a position of the stage 62 in the z direction (z coordinate) when the focal point of the objective lens 121 is positioned on the subject, for example.

If the culture observation apparatus 11 has a configuration for the objective lens 121 to move with respect to the fixed state 62, the focusing position of the objective lens 121 can be the position in the z direction of the objective lens 121 itself.

As a macro image, the macro image generation unit 164 generates one image in which the entire culture container 61 is displayed, out of the plurality of observation images obtained by imaging different positions of the culture container 61. The recording unit 165 is constituted by a nonvolatile memory, for example, and records programs which the control unit 38 executes, various data and observation images. A macro image is also recorded in the recording unit 165, but instead of the macro image, each of a plurality of observation images obtained by imaging different positions of the culture container 61 may be directly recorded in the recording unit 165. In other words, each of the plurality of observation images constituting a macro image may be recorded.

If the observer operates the touch panel 151 and starts observing a fertilized embryo in a culture container 61 stored in a predetermined rack of the stocker 34, the control unit 38 moves the culture container 61 specified by the observer onto the stage 62. In other words, the observation control unit 162 controls the container transporting mechanism 35 according to the signal from the touch panel 151, and the container transporting mechanism 35 transports the culture container 61 stored in the stocker 34 according to this control, and places it on the stage 62.

If the culture container 61 specified by the observer is placed on the stage 62, the culture observation apparatus 11 starts the observation processing to observe the fertilized embryo in the culture container 61. Now the observation processing will be described with reference to the flow chart in FIG. 5.

In step S11, the container observation unit 102 captures an image of the entire culture container 61 on the stage 62.

In other words, the observation control unit 162 controls the stage 62 and moves the stage 62 so that the culture container 61 on the stage 62 is placed on the optical path of the illumination light from the second illumination unit 104. Then the observation control unit 162 irradiates the illumination light on the second illumination unit 104, and causes the container observation unit 102 to capture an observation image of the entire culture container 61 as the subject. If the observation image is captured, the control unit 38 obtains the observation image from the container observation unit 102, supplies it to the display unit 36, and displays the observation image.

In step S12, the control unit 38 accepts the specification on a detection area including a subject to be observed, in the observation image displayed on the display unit 36.

In other words, if the observation image is displayed on the display unit 36, the observer performs input operation on the display screen of the display unit 36, and specifies an area which is on the displayed observation image, and which includes the subject to be observed, as the detection area. The control unit 38 selects the area specified by the observer as the detection area, based on the signal from the touch panel 151.

For example, it is assumed that some culture medium drops containing a fertilized embryo to be observed are located in the bottom of the culture container 61, and the culture container 61 is filled with a colorless and transparent mineral oil. And it is assumed that the observation image shown in FIG. 6 is displayed on the display unit 36 as the observation image captured by the container observation unit 102 in this case.

Figure 6:
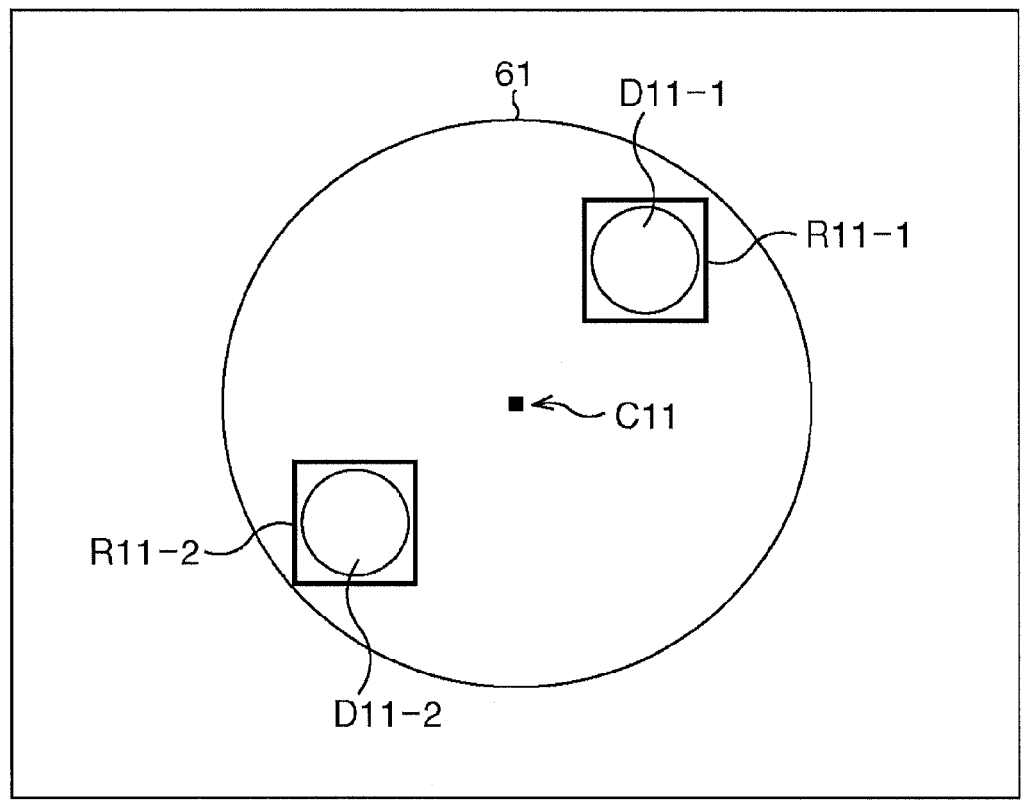
FIG. 6 is a diagram depicting culture medium drops in a culture container to be an observation target.

In the example in FIG. 6, a circular culture container 61 is displayed at the center of the observation image, and the position indicated by the arrow C11 is a center position on the bottom of the culture container 61 (hereafter called "center position C11"). Two culture medium drops D11-1 and D11-2 are formed in the culture container 61.

In FIG. 6, the culture medium drop D11-1 is located in an upper right direction when viewed from the center position C11, and the culture medium drop D11-2 is located in the lower left direction when viewed from the center position C11. The observer specifies the detection areas, for example, to an area R11-1 which is around the culture medium drop D11-1 and includes the entire culture medium drop D11-1, and an area R11-2, which is around the culture medium drop D11-2 and includes the entire culture medium drop D11-2.

Hereafter, the culture medium drop D11-1 and the culture drop D11-2 may be simply called "culture medium drop D11", when clear distinction is not required, and the area R11-1 and the area R11-2 may be simply called "area R11" when clear distinction is not required.

Figure 7:
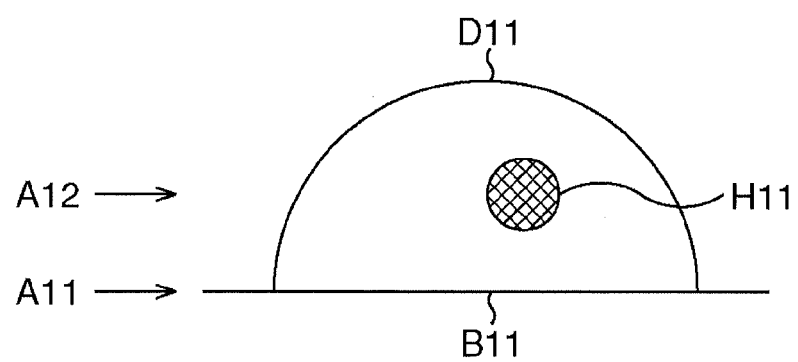
FIG. 7 is a diagram depicting a culture medium drop and a fertilized embryo.

The culture medium drop D11 formed in the culture container 61 has a certain thickness in the z direction, as shown in FIG. 7, for example. In FIG. 7, the vertical direction indicates the z direction, that is, the optical axis direction of the objective lens in a container observation unit 102 and the objective lens 121.

In the example in FIG. 7, a hemispherical culture medium drop D11 is formed on the bottom B11 of the culture container 61, and one fertilized embryo H11 to be observed is floating in the culture medium drop D11. The culture medium drop D11 does not move with respect to the bottom B11, but the fertilized embryo H11 moves in any direction in the culture medium drop D11.

Therefore in the culture observation apparatus 11, when the focusing position of the objective lens 121 on the fertilized embryo H11 is detected, the focusing position of the objective lens 121 on the culture medium drop D11 is detected first by auto focus control. In other words, a position of the stage 62 in the z direction, by which the position of the focal point of the objective lens 121 in the z direction comes to a boundary between the boundary portion (edge portion) of the culture medium drop D11 and the bottom B11 of the culture container 61 indicated by arrow A11, is detected.

Then by auto focus control based on the focusing position on the culture medium drop D11, a position of the stage 62 in the z direction, by which the focusing position of the objective lens 121 on the fertilized embryo H11, that is, the position of the focal point of the objective lens 121 in the z direction, comes to the center of the fertilized embryo H11 indicated by the arrow A12, is detected.

Compared with detecting a focusing position on the moving fertilized embryo H11, detecting a focusing position on the culture medium drop D11, which does not move, is relatively easier, and if the focusing position on the fertilized embryo H11 is detected, based on the focusing position on the culture medium drop D11, the focusing position on the fertilized embryo H11 can be detected with more certainty.

The fertilized embryo H11 floats in the culture medium drop D11, but is often located near the bottom B11 of the culture container 61 in the culture medium drop D11. Therefore if the focusing position on the culture medium drop D11, that is, as shown in the figure, the bottom B11, is used as a reference and the detection target is limited to the predetermined distance range upward from the bottom B11, then the focusing position on the fertilized embryo H11 can be detected with more certainty than the case of detecting the focusing position on the fertilized embryo H11 without setting any reference position, as is the case of the prior art.

Hereafter, the boundary portion between the boundary (surface) portion of the culture medium drop D11 and the bottom B11 of the culture container 61, that is, a portion where the hemispherical surface of the culture medium drop D11 and the bottom B11 meet in FIG. 7, is called "edge portion of the culture medium drop D11".

Figure 5:
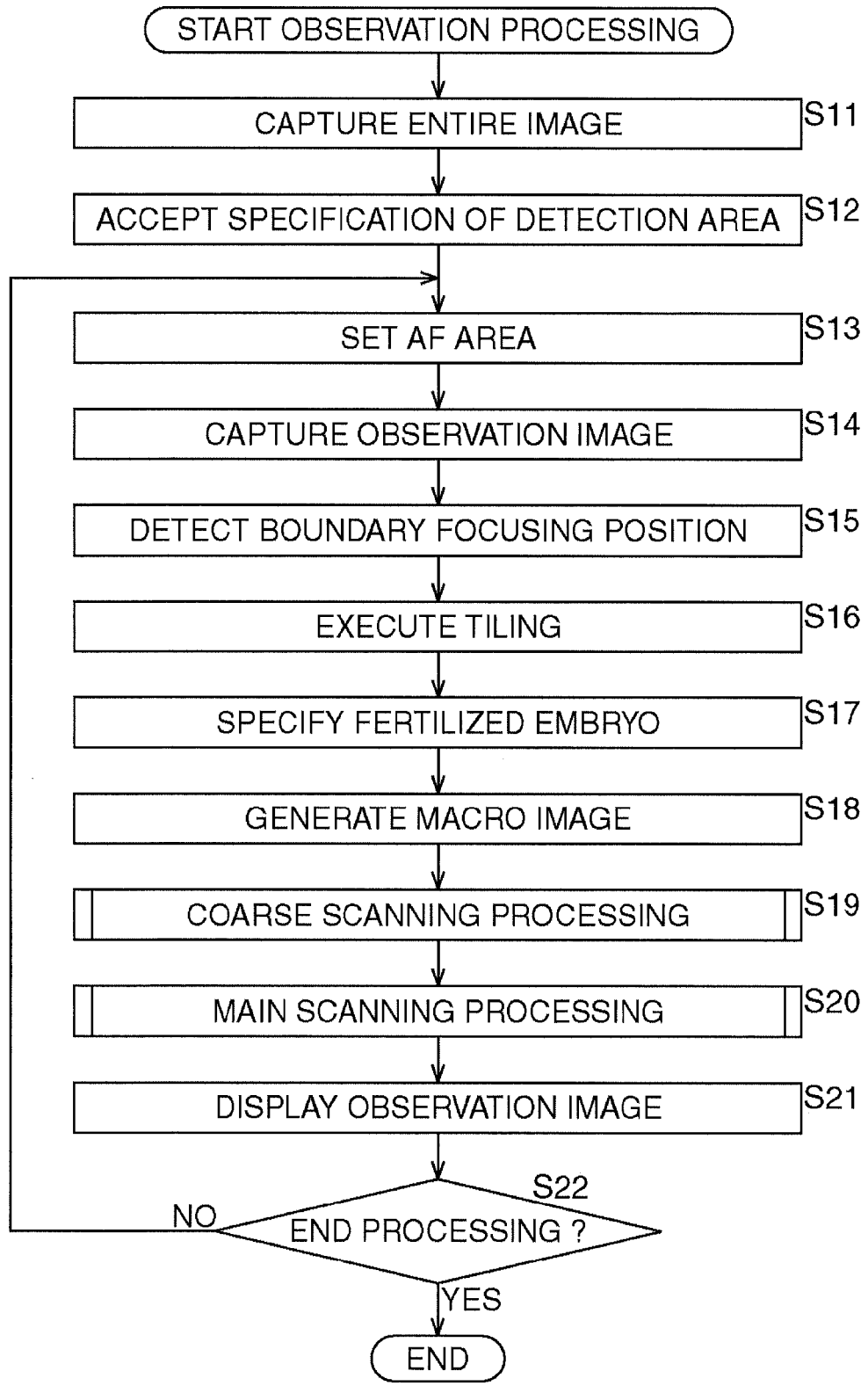
FIG. 5 is a flow chart depicting the observation processing.

Referring back to the flow chart in FIG. 5, when the observer specifies areas R11 in the observation image as the detection areas, the control unit 38 selects one of the specified detection areas as the processing target detection area.

In step S13, the area setting unit 161 of the control unit 38 sets an AF area for the culture medium drop in the processing target detection area.

If the culture medium drop D11 in the processing target detection area is on the right side of the center position C11 in FIG. 6, for example, the area setting unit 161 sets an area having a predetermined size, of which center is the center position of the left hand side of the rectangular area R11 selected as the detected area, as the AF area.

The size of the AF area is set to a size by which the edge portion of the culture medium drop D11 is included in the AF area. The edge portion of the culture medium drop D11 must be included in the AF area here because the focusing position is detected based on the contrast intensity of the edge portion.

Figure 8:
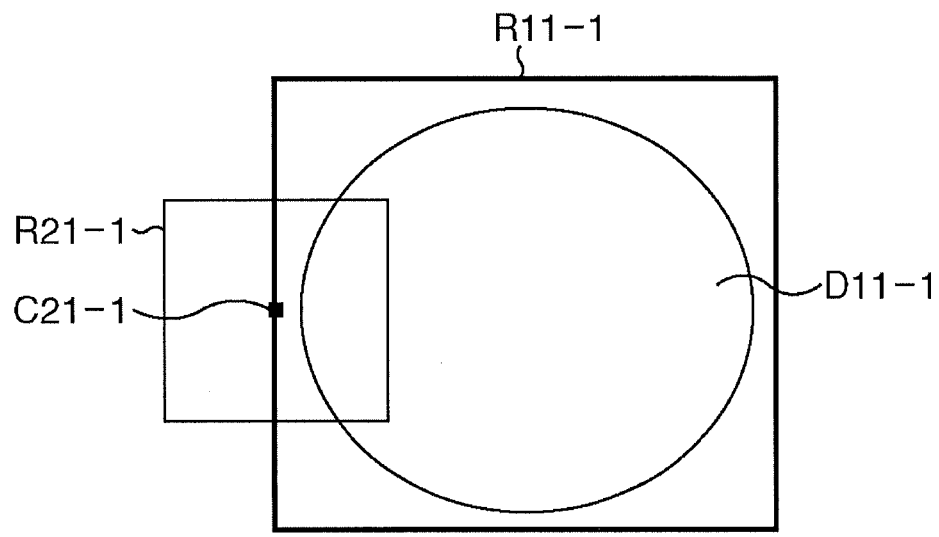
FIG. 8 is a diagram depicting an AF area.

In concrete terms, if the area R11-1 in FIG. 6 is selected as a processing target detection area, an area R21-1 having a predetermined size, of which center is the center position C21-1 of the left hand side of the area R11-1, as shown in FIG. 8, is selected as the AF area. The area R21-1 includes the left side edge portion of the culture medium drop D11-1, as shown in FIG. 8.

If the culture medium drop D11 in the processing target detection area is on the left side of the center position C11 in FIG. 6, for example, the area setting unit 161 sets an area having a predetermined size, of which center is the center position of the right hand side of the rectangular area R11 selected as the detection area, as the AF area. The size of the AF area is set to a size by which the edge portion of the culture medium drop D11 is included in the AF area.

Figure 9:
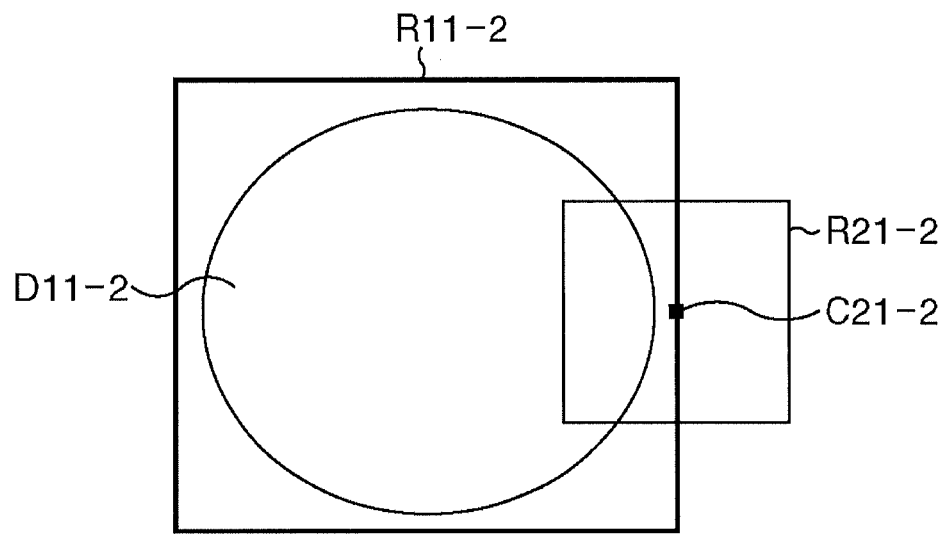
FIG. 9 is a diagram depicting an AF area.

In concrete terms, if the area R11-2 in FIG. 6 is selected as a processing target detection area, an area R21-2 having a predetermined size, of which center is the center position C21-2 of the right hand side of the area R11-2, as shown in FIG. 9, is selected as the AF area. The area R21-2 includes the right side edge portion of the culture medium drop D11-2, as shown in FIG. 9.

Hereafter the position C21-1 and the position C21-2 may be simply called "position C21" when a clear distinction is not required, and the area R21-1 and the area R21-2 may be simply called "area R21" when clear distinction is not required.

By setting the position C21, on the boundary on the center position C11 side of the area R11 selected as the detection area, to the center, and selecting the area R21 which includes the edge portion of the culture medium drop D11 as the AF area, as described above, the focusing position on the culture medium drop D11 can be detected more easily and with certainty.

For example, the focusing position is normally detected by capturing a plurality of observation images while changing the distance from the objective lens 121 to the stage 62, and detecting an observation image of which contrast intensity is highest, out of those observation images. In other words, a position of the objective lens 121, when an observation image having the highest contrast intensity is captured, is regarded as the focusing position of the objective lens 121 on the subject.

In an area near the edge of the culture container 61, that is, in an area near the side wall face of the culture container 61, illumination unevenness, that is brightness unevenness, is generated since the illumination light irradiated onto the culture container 61 is eclipsed by the side wall face. If such illumination unevenness is generated, contrast is changed by the illumination unevenness, hence if an area including the illumination unevenness is used as an AF area, error occurs in detecting a focusing position of the objective lens 121 on the subject, and accuracy to detect the focusing position drops.

Therefore the culture observation apparatus 11 selects an area on the center position C11 side of the culture container 61 when viewed from the culture medium drop D11, as an AF area so that the area which causes a detection error is not included in the AF area. As a result, a focusing position on the subject (culture medium drop D11) can be detected more easily and with certainty.

An area to be selected as the AF area can be any area which includes the edge portion of the culture medium drop D11, and which does not generate illumination unevenness.

Therefore if illumination unevenness is generated only in an area which is within a predetermined distance L from the side wall face of the culture container 61, for example, an area, which does not include the area within the distance L from the side wall face of the culture container 61 and which includes the edge portion of the culture medium drop D11, is selected as the AF area.

Referring back to the flow chart in FIG. 5, when the AF area is set, the observation control unit 162 controls the microscopic observation unit 103, and moves the objective lens 121-1 and the intermediate zoom lens 122-1 so that the objective lens 121-1 and the intermediate zoom lens 122-1 are disposed on the phase contrast observation optical path.

The observation control unit 162 also controls the stage 62 and moves the stage 62 so that the culture container 61 on the stage 62 is disposed on the phase contrast observation optical path. To be more specific, the observation control unit 162 moves the stage 62 so that the center position of the AF area, determined with respect to the detection area to be the processing target, comes to a position on the phase contrast observation optical path. In this case, the entire observation field of view of the objective lens 121 becomes the AF area. In other words, the entire observation image becomes the AF area.

Then the observation control unit 162 controls the first illumination unit 101 and irradiates the illumination light onto the culture container 61. Thereby the phase contrast observation on the culture container 61 becomes possible at ×2 optical magnification.

In step S14, the observation control unit 162 causes the camera 124 to capture the observation image at each position of the stage 62, while moving the stage 62 in the z direction. In other words, the illumination light irradiated from the first illumination unit 101 onto the AF area of the culture container 61 transmits through the AF area (e.g. culture medium drop), and enters the objective lens 121-1.

The illumination light which entered the objective lens 121-1 is collected by the objective lens 121-1, and enters the camera 124 via the intermediate zoom lens 122-1 and the image optical system 123. The camera 124 performs photo-electric conversion on the illumination light which entered from the image optical system 123 along with the movement of the stage 62, so as to capture observation images of the area which includes the AF area.

Since an observation image in each state, when the stage 62 is located at each position in the z direction, is obtained like this, the control unit 38 obtains a plurality of observation images captured by the camera 124.

In step S15, the focal point position detection unit 163 detects a focusing position of the objective lens 121-1 on the culture medium drop (hereafter especially called "boundary focusing position"), based on the plurality of observation images obtained by the camera 124. In other words, the focal point position detection unit 163 determines the contrast intensity of each of the plurality of observation images, and regards the position of the stage 62 in the z direction, when the observation image having the highest contrast intensity was captured, as the boundary focusing position.

The boundary focusing position detected like this is a position of the stage 62 when the focal position of the object lens 121-1 is at a boundary between the edge portion of the culture medium drop and the bottom of the culture container 61.

When an observation image for detecting the boundary focusing position is captured, it is preferable to use a high NA (Numerical Aperture) optical system of which depth of focus is small, so that the edge portion of the culture medium drop can be accurately detected.

In step S16, the observation control unit 162 performs tiling. In other words, the observation control unit 162 controls the microscopic observation unit 103, and moves the objective lens 121-2 and the intermediate zoom lens 122-2 so that the objective lens 121-2 and the intermediate zoom lens 122-2 are disposed on the phase contrast observation optical path. Thereby the phase contrast observation on the culture container 61 becomes possible at ×4 optical magnification.

To be more specific, when the objective lens 121 is switched, the stage 62 is moved based on the control of the observation control unit 162, so that the focal position of the objective lens 121-2 after switching becomes the boundary position between the edge portion of the culture medium drop and the bottom of the culture container 61.

Then the observation control unit 162 causes the camera 124 to capture an observation image at each position of the stage 62, while moving the stage 62 in the xy directions, so that all the areas of the processing target detection area is captured by a plurality of times of image capturing.

Figure 10:
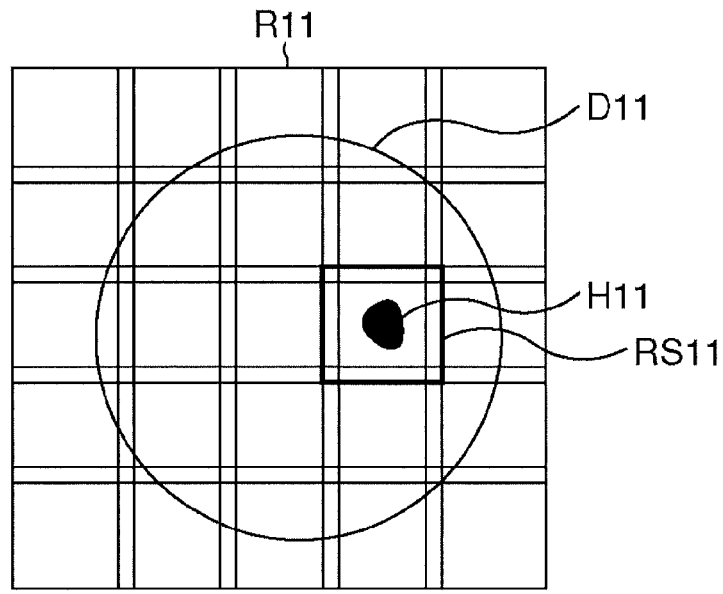
FIG. 10 is a diagram depicting tiling.

In this way the entire area R11, which was selected as the detection area, is captured by a plurality of times of image capturing, as shown in FIG. 10, for example. In FIG. 10, one square, such as the area RS11, indicates an area included in the observation image obtained by one image capturing.

In the case of the example in FIG. 10, the entire area R11 was imaged by a total of twenty five times of image capturing (five times in the vertical direction, and five times in the horizontal direction). Each observation image has portions that overlap with adjacent observation images. In other words, in the detection area, an area near the edges of one area imaged as an observation image, is also included in an area imaged as another observation image.

After an observation image of each area in the detection area is captured like this, the control unit 38 obtains this plurality of images from the camera 124.

In step S17, the macro image generation unit 164 specifies a position of the fertilized embryo (hereafter called "fertilized embryo position") in the detection area based on the observation image of each area of the detection area obtained by tiling. For example, for each observation image, the macro image generation unit 164 determines a shape and size of an object included in the observation image, and determines whether this object is the fertilized embryo or not, whereby the fertilized embryo position in the detection area is specified.

For example, in the case of the example in FIG. 10, the fertilized embryo H11 exists in the area RS11 in the area R11 selected as the detection area, hence the fertilized embryo H11 is detected in the observation image of the area RS11, and the position of the fertilized embryo H11 is regarded as the fertilized embryo position.

In step S18, the macro image generation unit 164 generates one image by arranging each of the plurality of observation images obtained by tiling, so as to be the same positional relationship as the areas of the subject captured in these observation images, and regards this image as the macro image. In other words, a macro image is an image of the entire detection area generated by arranging and merging a plurality of observation images.

When observation images for generating a macro image are captured, it is preferable to use a low NA optical system, of which depth of focus is large, in order to decrease the focal shift on the entire detection area, particularly on the fertilized embryo.

In step S19, the culture observation apparatus 11 performs coarse scanning, and detects a general focusing position on the fertilized embryo in the processing target detection area. For example, in the coarse scanning processing, the area centering around the fertilized embryo position is selected as the AF area, and auto focus control is performed based on the focusing position on the culture medium drop. The coarse scanning processing will be described in detail later.

In step S20, the culture observation apparatus 11 performs the main scanning processing, and detects a more accurate focusing position on the fertilized embryo in the processing target detection area. For example, in the main scanning processing, an area centered around the fertilized embryo position is selected as the AF area, and auto focus control is performed based on the focusing position obtained in the coarse scanning processing. In the main scanning processing, an observation image at each position in the z direction of the stage 62 is captured, and these observation images, the fertilized embryo position, the focusing position of the objective lens 121 on the fertilized embryo, and the macro image are recorded in the recording unit 165. The main scanning processing will be described in detail later.

In step S21, the control unit 38 supplies the observation image, which was captured when the stage 62 (objective lens 121) is positioned in the finally determined focusing position of the objective lens 121 on the fertilized embryo, to the display unit 36, and causes the display unit 36 to display the observation image.

In step S22, the control unit 38 determines whether processing is ended or not. For example, it is determined that the processing is ended if all the plurality of detection areas, specified by the observer, become the processing targets, and the focusing position is detected.

If it is determined that the processing is not ended in step S22, the next detection area which has not yet been selected becomes the processing target, processing returns to step S13, and the above mentioned processing is repeated.

If it is determined that the processing is ended in step S22, on the other hand, the container transporting mechanism 35 transports the culture container 61 on the stage 62 to a rack of the stocker 34, according to the control of the observation control unit 162, and the observation processing ends.

As described above, the culture observation apparatus 11 selects an area, which includes an edge portion of the culture medium drop in the culture container 61 and has no illumination unevenness, as the AF area, and detects a boundary focusing position of the culture medium drop in the AF area as a detection target. Then the culture observation apparatus 11 detects a focusing position on the fertilized embryo, based on the boundary focusing position.

By detecting the boundary focusing position with selecting an area which includes an edge portion of the culture medium drop and has no illumination unevenness as the AF area in this way, the boundary focusing position of the objective lens 121 on the culture medium drop can be detected more simply and with certainty. If the focusing position on the fertilized embryo position is detected based on this boundary focusing position, the final focusing position on the fertilized embryo can be detected more simply and with certainty.

The coarse scanning processing corresponding to the processing in step S19 in FIG. 5 will now be described with reference to the flow chart in FIG. 11.

In step S51, the observation control unit 162 changes the optical magnification to observe the culture container 61 in the observation unit 37.

In other words, the observation control unit 162 controls the microscopic observation unit 103 and moves the objective lens 121-3 and the intermediate zoom lens 122-3 so that the objective lens 121-3 and the intermediate zoom lens 122-3 are disposed on the phase contrast observation optical path.

The observation control unit 162 also changes the setting of the camera 124 so that the resolution of the observation image is decreased by binning, and controls the first illumination unit 101, to irradiate the illumination light onto the culture container 61. Thereby the phase contrast observation for the culture container 61 becomes possible at ×10 optical magnification. The optical magnification need not be ×10 if the fertilized embryo is included in the entire observation image, and can be a magnification which the observer specified in advance, for example.

Then the observation control unit 162 controls the stage 62 and moves the stage 62 in the xy directions so that the fertilized embryo position specified in step S17 in FIG. 5 is located on the phase contrast observation optical path. At the same time, the observation control unit 162 controls the stage 62, and moves the stage 62 so that the position of the stage 62 in the z direction comes to the boundary focusing position detected in step S15 in FIG. 5.

As a result, the focal position of the objective lens 121 in the xy directions becomes the same as the position of the fertilized embryo, and the position [of the focal position of the objective lens 121] in the z direction comes to the position on the boundary surface between the culture medium drop and the bottom of the culture container 61. Therefore if the stage 62 (objective lens 121) is moved in the z direction in this state, the fertilized embryo can be focused on.

Figure 12:
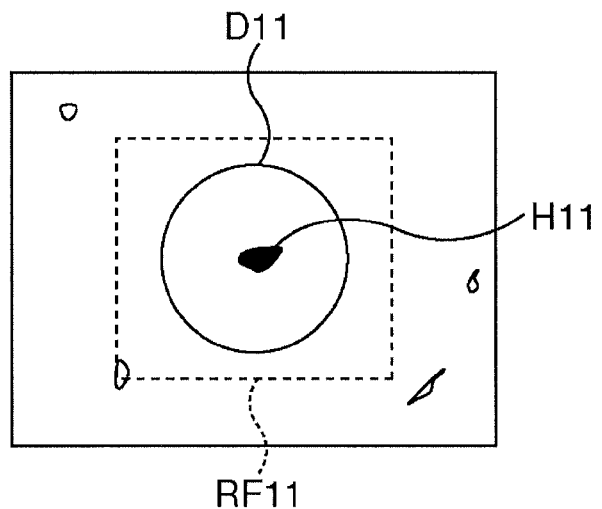
FIG. 12 is a diagram depicting an AF area.

Then the area setting unit 161, as shown in FIG. 12, sets the AF area to an area RF11 around the culture medium drop D11, of which center is the fertilized embryo position and which includes the entire culture medium drop D11. This area RF11 is determined so that the area RF11 has a boundary in a position close to the boundary of the culture medium drop D11, and the culture medium drop D11 occupies most of the area RF11.

By selecting the area RF11 around the culture medium drop D11, which includes the entire culture medium drop D11, as the AF area like this, the focusing position on the fertilized embryo can be detected with more certainty. In other words, foreign substances exist in the culture container 61 along with the culture medium drops D11, therefore if the AF area is too large, many foreign substances are included in the AF area, and accuracy to detect the focusing position diminishes. By selecting the area around the culture medium drop D11 as the AF area, foreign substances included in the AF area can be minimized, and the focusing position can be detected more accurately.

Figure 11:
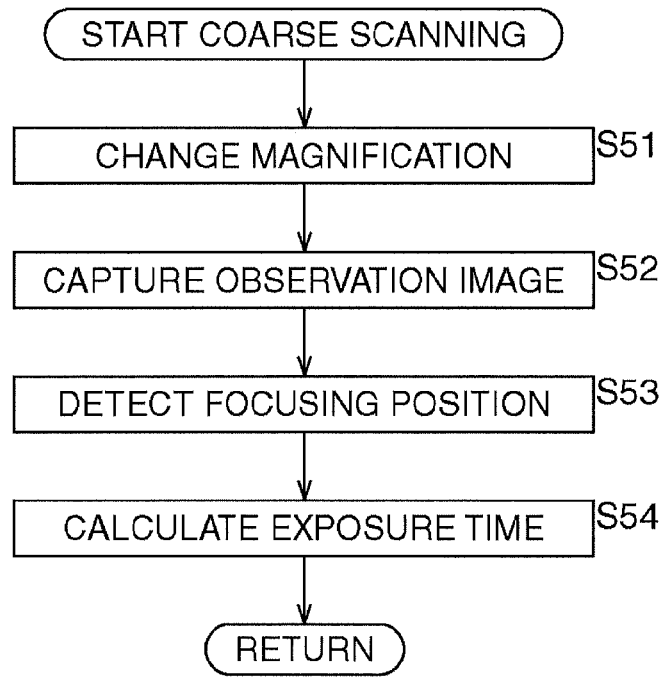
FIG. 11 is a flow chart depicting a coarse scanning processing.

Referring back to the flow chart in FIG. 11, in step S52, the observation control unit 162 causes the camera 124 to capture the observation image at each position of the stage 62, while moving the stage 62 in the z direction from the boundary focusing position. In other words, the illumination light from the first illumination unit 101 enters the camera 124 via the culture container 61, the stage 62, the objective lens 121-3, the intermediate zoom lens 122-3 and the image optical system 123, and the observation images are captured by the camera 124.

For example, the focal position of the objective lens 121 in the z direction is moved from the position indicated by the arrow A11 in FIG. 7 (state where the stage 62 is in the boundary focusing position) to a predetermined position above the position indicated by the arrow A12 in FIG. 7 (area near the upper edge portion of the culture medium drop D11). Then an observation image is captured in each state where the objective lens 121 is located at each position in the z direction.

If the stage 62 is moved to each position in a predetermined range in the z direction including the boundary focusing position, an observation image is captured in a state where the stage 62 is at each position, and a focusing position on the fertilized embryo is detected like this, then detection accuracy can be improved. The range of moving the stage 62 (objective lens 121) in the z direction must be a relatively wide range, sufficient to focus on the fertilized embryo without fail.

After the observation images are captured at each position in the z direction, the control unit 38 obtains a plurality of observation images captured by the camera 124. The captured observation image is sufficient if the AF area is included, and it is unnecessary that the observation field of view of the objective lens 121-3 and the AF area match.

Referring back to the flow chart in FIG. 11, in step S53, the focal position detection unit 163 detects the focusing position of the objective lens 121-3 on the fertilized embryo, based on the plurality of observation images obtained by the camera 124 (hereafter especially called "tentative fertilized embryo focusing position").

In other words, the focal position detection unit 163 determines the contrast intensity in each AF area of the plurality of observation images, and regards a position of the stage 62 in the z direction, when an observation image having a maximum contrast intensity is captured, as the tentative fertilized embryo focusing position.

The tentative fertilized embryo focusing position detected like this is a position of the stage 62 in the z direction when the focal position of the objective lens 121-3 is in the position of the fertilized embryo. In the coarse scanning processing however, only a certain degree of detection accuracy can be implemented, since observation images at low resolution are used for detection.

In step S54, the observation control unit 162 calculates the exposure time of the camera 124, which is set for executing the main scanning processing, using the observation image captured in a state where the stage 62 is located in the tentative fertilized embryo focusing position. For example, the observation control unit 162 determines the brightness value of each pixel of the entire observation image, and determines the exposure time by multiplying the average value of these brightness values by a predetermined coefficient.

The exposure time calculated like this is suitable for imaging the fertilized embryo as a subject. In other words, the brightness around the fertilized embryo upon capturing an observation image greatly changes depending on the position in the culture medium drop where the fertilized embryo exists, hence the exposure time must be set appropriately.

Here the state where the stage 62 is in the tentative fertilized embryo focusing position is a state where the fertilized embryo is generally focused, and in the observation image captured in this state, the fertilized embryo to be the subject is at the center of the image. In other words, the observation image captured in this state is an image captured in an environment which is approximately the same as the observation image which is captured in a state where the fertilized embryo is more accurately focused in the main scanning processing. Therefore using an observation image captured in a state where the fertilized embryo is generally focused, an exposure time suitable for the image capturing environment is calculated, and imaging is performed with the calculated exposure time in the main scanning, then an observation image with more appropriate brightness can be obtained.

After the exposure time is calculated like this, the coarse scanning processing ends, and processing advances to step S20 in FIG. 5.

By detecting the focusing position on the fertilized embryo based on the focusing position on the culture medium drop like this in the coarse scanning processing, a general focusing position on the fertilized embryo can be obtained with more certainty. Furthermore only the area around the fertilized embryo is used as the AF area, hence the accuracy to detect the focusing position can be increased even more.

Now the main scanning processing corresponding to the processing in step S20 in FIG. 5 will be described with reference to the flow chart in FIG. 13.

In step S81, the observation control unit 162 changes the setting for observing the culture container 61 in the observation unit 37. In other words, the observation control unit 162 changes the setting of the camera 124, so that the exposure time of the camera 124 is changed to the exposure time calculated in the processing in step S54 in FIG. 11, and the resolution of the observation image becomes higher than that in the coarse scanning processing.

The observation control unit 162 also controls the first illumination unit 101, and irradiates the illumination light onto the culture container 61. Thereby the phase contrast observation for the culture container 61 becomes possible at ×10 optical magnification.

Then the observation control unit 162 controls the stage 62 and moves the stage 62 in the xy directions so that the fertilized embryo position specified in step S17 in FIG. 5 is located on the phase contrast observation optical path. At the same time, the observation control unit 162 controls the stage 62, and moves the stage 62 so that the position of the stage 62 in the z direction comes to the tentative fertilized embryo focusing position detected in step S53 in FIG. 11.

As a result, the focal position of the objective lens 121 becomes approximately the same as the position of the fertilized embryo. Therefore the fertilized embryo can be more accurately focused by moving the stage 62 from this state within a relatively narrow range in the z direction, centering around the tentative fertilized embryo focusing position.

Then the area setting unit 161 sets the AF area to an area around the culture medium drop, of which center is the fertilized embryo position and which includes the entire culture medium drop, just like the case of the coarse scanning processing. This AF area is the same area as the AF area used for the coarse scanning processing.

In step S82, the observation control unit 162 causes the camera 124 to capture an observation image at each position of the stage 62, while moving the stage 62 from the tentative fertilized embryo focusing position in the z direction. In other words, the illumination light from the first illumination unit 101 enters the camera 124 via the culture container 61, the stage 62, the objective lens 121-3, the intermediate zoom lens 122-3 and the image optical system 123, and the observation image is captured by the camera 124.

For example, the focal position of the objective lens 121 in the z direction is moved from the position indicated by the arrow A12 in FIG. 7 to each position in the predetermined range centering around the position. Then an observation image is captured in each state where the objective lens 121 is located at each position in the z direction. In other words, the stage 62 is moved to each position in the predetermined range centering around the tentative fertilized embryo focusing position, and an observation image is captured.

If the stage 62 is moved to each position in a predetermined range in the z direction centering around the tentative fertilized embryo position, an observation image is captured in a state where the stage 62 is at each position, and a focusing position on the fertilized embryo is detected like this, then a more accurate focusing position can be detected.

In the main scanning processing, the range of moving the objective lens 121 (stage 62) in the z direction is narrower than the range of moving the objective lens 121 in the coarse scanning processing. This is because the general focusing position on the fertilized embryo has been detected in the coarse scanning processing, and the detection target can only be an area around this focusing position.

If the observation image at each position in the z direction is captured, the control unit 38 obtains a plurality of observation images captured by the camera 124. The captured observation image is sufficient if the AF area is included.

Figure 13:
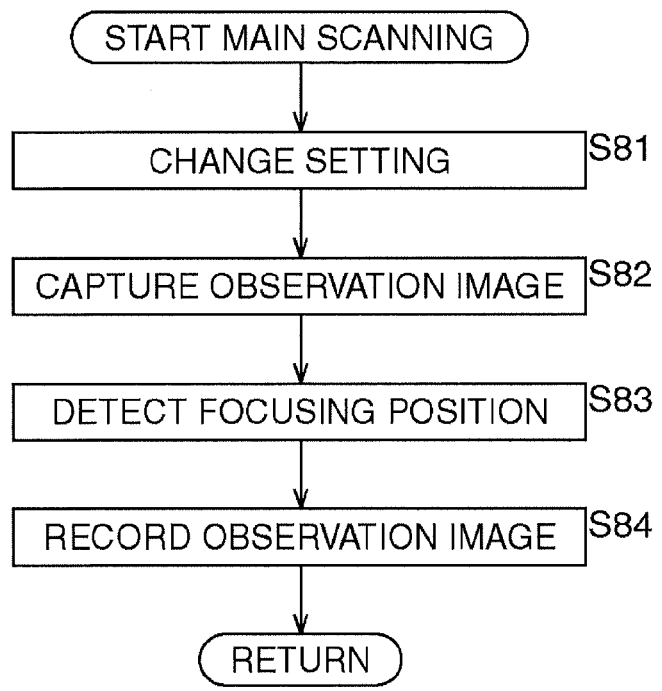
FIG. 13 is a flow chart depicting the main scanning processing.

Referring back to the flow chart in FIG. 13, in step S83, the focal point detection unit 163 detects the focusing position of the objective lens 121-3 on the fertilized embryo (hereafter especially called "final fertilized embryo focusing position") based on the plurality of observation images obtained by the camera 124.

In other words, the focal position detection unit 163 determines the contrast intensity in each AF area of the plurality of observation images, and regards the position of the stage 62 in the z direction when an observation image having the highest contrast intensity was captured as the final fertilized embryo focusing position.

The final fertilized embryo focusing position detected like this is a position of the stage 62 when the focal position of the objective lens 121-3 comes to the position of the fertilized embryo. In this canning processing, observation images, having higher resolution than those in the coarse scanning, are used for detection, hence the final fertilized embryo focusing position should be a more accurate focusing position than the tentative fertilized embryo focusing position.

In step S84, the control unit 38 records the plurality of observation images captured in the main scanning processing, the final fertilized embryo focusing position, the fertilized embryo position and the macro image in the recording unit 165. To be more precise, the positions of the stage 62 in the x, y and z directions, upon capturing the observation image, are also recorded in correspondence with each observation image.

Out of the observation images recorded like this, the observation image captured in the final fertilized embryo focusing position is displayed on the display unit 36 in step S21 in FIG. 5. After the observation images and other data are recorded in the recording unit 165, the main scanning processing ends, and processing then advances to step S21 in FIG. 5.

In the main scanning processing, the focusing position on the fertilized embryo is detected based on the tentative fertilized embryo focusing position on the fertilized embryo, whereby the accurate focusing position on the fertilized embryo can be obtained more simply and with certainty. Furthermore, only the area around the fertilized embryo is used as the AF area, hence the accuracy to detect the focusing position can be increased even more.

In the above description, the observation processing is executed when the observer instructs a culture container 61 and observation of the culture container 61, but once the observer instructs the detection area, the observation processing is executed with a predetermined interval, regardless the instruction of the observer. In this case, each detection area previously specified sequentially becomes a processing target, and the observation images are captured in this area.

Embodiments of the present invention are not limited to the above embodiment, but numerous modifications can be made without departing from the true spirit and scope of the invention.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention, the scope of which is defined in the claims and their equivalents.

The invention claimed is:

1. A focus control method detecting a focusing position of a subject in a culture container, the method comprising:
executing a first imaging including generating an observation image by capturing an image of the culture container by an observation unit via an objective lens;
displaying the observation image on a display unit;
specifying a detection area which includes a subject in the culture container, from the observation image displayed on the display unit;
selecting and setting an AF area located outside an area that is within a predetermined distance from an edge of the culture container and including a boundary portion of the subject in the detection area; and
detecting a focal position, by a focal position detection unit, on the subject in the AF area.

2. The focus control method according to claim 1, wherein the AF area setting operation comprises selecting the AF area which includes a boundary portion of the subject located on the container center side of the subject.

3. The focus control method according to claim 1, comprising:
executing a focal adjustment operation of adjusting a relative distance between the objective lens and a stage in an optical axis direction and adjusting a focusing position of the objective lens; and
executing a second imaging operation of changing the relative distance from a focusing state after the adjustment of the focusing position of the objective lens, and imaging the detection area according to the change.

4. A culture observation apparatus having a microscope for observing a transparent culture container in which a culture medium drop is disposed, comprising:
an objective lens of the microscope;
an observation unit configured to image the culture container via the objective lens and generating an observation image, the observation unit having a camera;
a specification operation unit configured to specify a detection area which includes the culture medium drop in the culture container, from the observation image displayed on a display unit based on an input operation by an observer;
an area setting unit configured to select an AF area located outside an area that is within a predetermined distance from an edge of the culture container and include a boundary portion of the culture medium drop in the detection area; and
a focal position detection unit communicatively coupled with the microscope for detecting a focusing position on the culture medium drop in the AF area.

5. The culture observation apparatus according to claim 4, wherein the area setting unit selects the AF area which includes a boundary portion of the culture medium drop located on the container center side of the culture medium drop.

6. The culture observation apparatus according to claim 4, comprising:
a control unit communicatively coupled with the microscope for adjusting a relative distance between the objective lens and a stage in an optical axis direction, and adjusting a focusing position of the objective lens on a boundary portion of the culture medium drop, and
wherein the observation unit changes the relative distance in the optical axis direction of the objective lens according to the control of the control unit after the adjustment of the focusing position of the objective lens, and images the detection area according to the change.

7. A culture observation apparatus having a microscope for observing a transparent culture container in which a culture medium drop is disposed, comprising:
an objective lens of the microscope;
an observation unit for imaging the culture container via the objective lens and generating an observation image, the observation unit having a camera;
a specification operation unit for specifying a detection area which includes the culture medium drop in the culture container, from the observation image displayed on a display unit based on an input operation by an observer;
an area setting unit for selecting an AF area, which does not include an area located within a predetermined distance from an edge of the culture container and includes a boundary portion of the culture medium drop in the detection area;
a focal position detection unit communicatively coupled with the microscope for detecting a focusing position on the culture medium drop in the AF area; and
a control unit communicatively coupled with the microscope for adjusting a relative distance between the objective lens and a stage in an optical axis direction, and adjusting a focusing position of the objective lens on a boundary portion of the culture medium drop; and controlling the stage, on which the culture container is placed, so as to move in an XY direction, and
wherein the observation unit, after the control unit adjusts the focusing position of the objective lens, images each of a plurality of divided areas in the detection area while moving the stage in the XY direction by the control unit.

8. The culture observation apparatus according to claim 7, wherein
the observation unit detects a fertilized embryo included in the culture medium drop based on the observation image of each of the divided areas in the detection area, and
the control unit moves the objective lens or the stage in the optical axis direction for the area which includes the detected fertilized embryo, and the observation unit obtains an observation image at each moved position.

9. The culture observation apparatus according to claim 4, wherein the microscope performs phase contrast observation for the culture container.

10. The focus control method according to claim 1, wherein the observation image includes at least one subject in the culture container.

11. The focus control method according to claim 1, wherein the observation image includes a plurality of subjects in the culture container.

12. The focus control method according to claim 1, wherein the observation unit captures the image of the culture container in entirety.

13. The culture observation apparatus according to claim 4, wherein the observation unit images at least one subject in the culture container.

14. The culture observation apparatus according to claim 4, wherein observation unit images a plurality of subjects in the culture container.

15. The culture observation apparatus according to claim 4, wherein the observation unit images the culture container in entirety.

* * * * *